United States Patent [19]

Nandagiri et al.

[11] 4,164,562
[45] Aug. 14, 1979

[54] AEROSOL HAIR SPRAY CONTAINING AN ETHYL OR BUTYL MONOESTER OF A COPOLYMER OF MALEIC ACID AND A VINYL MONOMER

[75] Inventors: Arun Nandagiri, Lake Hiawatha; Uma Tripathi, Oakland; LeRoy Hunter, Randolph, all of N.J.

[73] Assignee: American Cyanamid Company, Stamford, Conn.

[21] Appl. No.: 844,241

[22] Filed: Oct. 21, 1977

[51] Int. Cl.$^2$ ............................................. A61K 7/11
[52] U.S. Cl. .................................. 424/47; 8/127.51; 252/305; 424/DIG. 1; 424/71
[58] Field of Search ..................... 424/DIG. 1, 47, 71; 8/127.51; 252/305

[56] References Cited

U.S. PATENT DOCUMENTS

| | | | |
|---|---|---|---|
| 2,723,248 | 11/1955 | Wright | 424/47 X |
| 3,790,664 | 2/1974 | Krochock et al. | 424/47 |
| 3,922,341 | 11/1975 | Abegg et al. | 424/47 |
| 3,972,336 | 8/1976 | Nowak et al. | 424/47 X |
| 4,036,241 | 7/1977 | Karg et al. | 424/47 X |

*Primary Examiner*—James O. Thomas, Jr.
*Assistant Examiner*—Vera C. Clarke
*Attorney, Agent, or Firm*—Charles J. Fickey

[57] ABSTRACT

A pressurized hair spray composition having reduced flammability, having from 20 to 35 percent aliphatic hydrocarbons and 2 to 12 percent water.

5 Claims, No Drawings

AEROSOL HAIR SPRAY CONTAINING AN ETHYL OR BUTYL MONOESTER OF A COPOLYMER OF MALEIC ACID AND A VINYL MONOMER

The present invention relates to pressurized, self-dispensing compositions to hold hair in place following combing or setting. More particularly, the invention relates to a pressurized hair spray composition having reduced flammability.

Pressurized hair sprays containing various resins suitable for holding hair in place are known. They include, for example, vinyl acetate-crotonic acid copolymers, polyvinylpyrrolidone, vinylpyrrolidone-vinyl acetate copolymers, and copolymers of methyl vinyl ether and monoethyl-or monobutyl esters of maleic acid. One such composition containing the latter resin is disclosed in U.S. Pat. No. 3,922,341 wherein an alcoholic solution of the resin is pressurized with trichlorofluoromethane, difluorodichloromethane and nitrous oxide.

Propellants containing the fluorinated hydrocarbons are widely known and used commercially. However, these fluorinated hydrocarbons are now held suspect in damaging the ozone layer of the stratosphere. Hydrocarbon propellants, for example, propane, n-butane, isobutane, and mixtures thereof, may be used in their place but such propellants are quite flammable and constitute a danger to the consumer.

The present invention provides a hair spray composition, utilizing the aliphatic hydrocarbon propellant, which is greatly reduced in flammability.

The present invention provides a composition comprising (a) 65 to 80 weight percent of a concentrated liquid phase and (b) 20 to 35 weight percent of an aliphatic hydrocarbon propellant. The liquid phase comprises by weight, based on the total weight of (a) and (b), from about 2 to 5 percent of a copolymer of a vinyl alkyl ether and a monoethylor monobutyl ester of maleic acid; from about 2 to 12 percent, preferably about 8 percent water; from about 0.1 to 0.3 percent of an organic base neutralizer for the free carboxyl groups of said copolymer; and ethanol or isopropanol, or a mixture thereof, to provide the remainder of the liquid phase.

The hydrocarbon propellant phase comprises propane, n-butane, isobutane, or mixtures thereof.

The resin used is a copolymer of the monoethyl- or monobutyl ester of maleic acid and a vinyl alkyl ether represented by the formula:

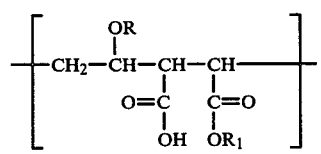

wherein R is an aliphatic radical containing 1 to 4 carbon atoms and $R_1$ is ethyl or butyl.

Among the vinyl alkyl ethers useful in preparing the resins may be mentioned methyl vinyl ether and butyl vinyl ether. Methyl vinyl ether is preferred. They are prepared to conventional polymerization methods as described in German Pat. No. 571,665 and in French Pat. No. 1,604,705. They have molecular weights in the range 15,000 to 60,000 and a viscosity between about 1.5 and 6 centipoises (5% solution in dimethylformamide at 34° C.). Resins representative of the above class which are commercially available include the monoethyl ester of the methyl vinyl ether-maleic acid copolymer available as Gantrez ES-225 and the butyl monoester of the methyl vinyl ether-maleic acid copolymer available as Gantrez ES-425. These products are available from General Aniline and Film Corp. as 50% solutions in ethanol or isopropanol. The polymers are not water-soluble.

The addition of from about 2 to 12 percent water to the alcoholic solution of the resin greatly reduces the flammability of the composition. Since the polymers are not water-soluble, the amount of water used is critical. Below about 2 percent there is very little noticeable effect on the flammability; above about 12 percent the polymer will precipitate from solution. Preferred results are obtained by the addition of about 8 percent water.

The free carboxyl groups of the polymer are partially neutralized by the addition of from about 0.1 to 0.3 percent of an organic base. Suitable bases include ammonia, dimethylamine, diethylamine, triethanolamine, triisopropanolamine, 2-methyl-2-amino-1-propanol, and the like. The latter is preferred. The addition of 0.1 to 0.3 percent of the base represents about a 10% to 25% rate of neutralization of the free carboxyl groups.

The alcohol used may be ethanol or isopropanol or a mixture thereof.

The aerosol compositions may contain, in addition to the foregoing ingredients, other cosmetic adjuvants, such as fragrance, colorants, plasticizers, etc.

The following examples illustrate the invention:

EXAMPLE 1

An aerosol hair spray is prepared by mixing the following ingredients:

| Ingredient | % |
|---|---|
| Gantrez ES-425* (50% solution in ethanol | 6.000 |
| Ethanol | 60.734 |
| Water | 8.000 |
| 2-Amino-2-methyl-1-propanol | 0.114 |
| Fragrance | 0.152 |
| Hydrocarbon A-31 (isobutane) | 25.000 |
| | 100.000 |

*Copolymer of the monobutyl ester of maleic acid and methyl vinyl ether

EXAMPLE 2

A hair spray was prepared containing the following ingredients:

| Ingredient | % |
|---|---|
| Gantrez ES-425 | 6.500 |
| Ethanol | 56.224 |
| Fragrance | 0.152 |
| 2-Amino-2-methyl-1-propanol | 0.124 |
| Propellant A-40* | 25.000 |
| Methylene chloride | 12.000 |
| | 100.000 |

*90% isobutane - 10% propane

The composition of Example 1 is about 25% less flammable than the composition of Example 2.

We claim:

1. A hair spray composition consisting essentially of (a) about 65 to 80 percent by weight of a liquid concentrate phase and (b) about 20 to 35 percent by weight of a lighter hydrocarbon propellant phase comprising propane, n-butane, isobutane, or mixtures thereof; said liquid concentrate phase comprising, based on the total weight of (a) and (b), from about 2 to 5 percent by weight of a film-forming carboxylic acid containing polymeric material which is a copolymer of an alkyl vinyl ether and the monoethyl- or monobutyl ester of maleic acid; from about 2 to 12 percent by weight water; from about 0.1 to 0.3 weight percent of an organic base neutralizer for said carboxylic acid-containing polymeric material; and sufficient amount of a material selected from the group consisting of ethanol, isopropanol, or mixtures thereof, to total 100 percent.

2. A composition according to claim 1 wherein said polymeric material is a copolymer of methyl vinyl ether and the monoethyl- or monobutyl ester of maleic acid in which at least about 10 percent of the free carboxylic acid groups are neutralized with an organic base.

3. A composition according to claim 2 wherein said organic base is selected from the group consisting of ammonia, dimethylamine, diethylamine, triethanolamine, triisopropanolamine and 2-methyl-2-amino-1-propanol.

4. A composition according to claim 3 wherein said organic base is 2-methyl-2-amino-1-propanol.

5. A composition according to claim 1 wherein said liquid concentrate phase contains about 8 percent water.

* * * * *